United States Patent
Fritze et al.

(10) Patent No.: US 8,722,672 B2
(45) Date of Patent: May 13, 2014

(54) TOPICAL PHARMACEUTICAL COMPOSITION INCLUDING REL-N-[6-[(2R,6S)-2,6-DIMETHYL-4-MORPHOLINYL]-3-PYRIDINYL]-2-METHYL-4'-(TRIFLUOROMETHOXY)-[1,1'-BIPHENYL]-3-CARBOXAMIDE

(75) Inventors: Andreas Fritze, Loerrach (DE); Karine Corcelle, Kembs (FR); Melinda Eniko Grubesa, Basel (CH)

(73) Assignee: Novartis AG, Basel (CH)

( * ) Notice: Subject to any disclaimer, the term of this patent is extended or adjusted under 35 U.S.C. 154(b) by 204 days.

(21) Appl. No.: 13/386,125

(22) PCT Filed: Jul. 20, 2010

(86) PCT No.: PCT/EP2010/060470
§ 371 (c)(1),
(2), (4) Date: Jan. 20, 2012

(87) PCT Pub. No.: WO2011/009852
PCT Pub. Date: Jan. 27, 2011

(65) Prior Publication Data
US 2012/0122866 A1 May 17, 2012

Related U.S. Application Data

(60) Provisional application No. 61/227,141, filed on Jul. 21, 2009, provisional application No. 61/295,884, filed on Jan. 18, 2010.

(51) Int. Cl.
*C07D 413/04* (2006.01)
*A61K 31/5377* (2006.01)
*A61P 35/00* (2006.01)
*A61P 17/06* (2006.01)
*A61P 17/00* (2006.01)

(52) U.S. Cl.
USPC ............... 514/235.5; 546/282.1; 546/307; 546/308; 546/312

(58) Field of Classification Search
USPC ............ 514/235.5; 546/282.1, 307, 308, 312
See application file for complete search history.

(56) References Cited

FOREIGN PATENT DOCUMENTS

| CN | 101445508 A | 6/2009 |
|---|---|---|
| WO | WO2007/131201 A2 | 11/2007 |
| WO | WO2008/154259 A1 | 12/2008 |

OTHER PUBLICATIONS

Jia Yiqun, et.al.,2007, "Identification of Food Additives and Pharmaceutical Excipient by Mass Spectrometry and Infrared Spectrum", p. 498, Jilin University Publishing Company, 1st edition.

*Primary Examiner* — Sreeni Padmanabhan
*Assistant Examiner* — Irina Neagu
(74) *Attorney, Agent, or Firm* — Matthew Mulkeen

(57) ABSTRACT

The present invention relates to pharmaceutical compositions of 2-Methyl-4'-trifluoromethoxy-biphenyl-3-carboxylic acid [6-(cis-2,6-dimethyl-morpholin-4-yl)-pyridin-3-yl]-amide, to the use of such compositions in therapeutic applications and to methods for manufacturing such compositions.

3 Claims, 2 Drawing Sheets

FIG 1
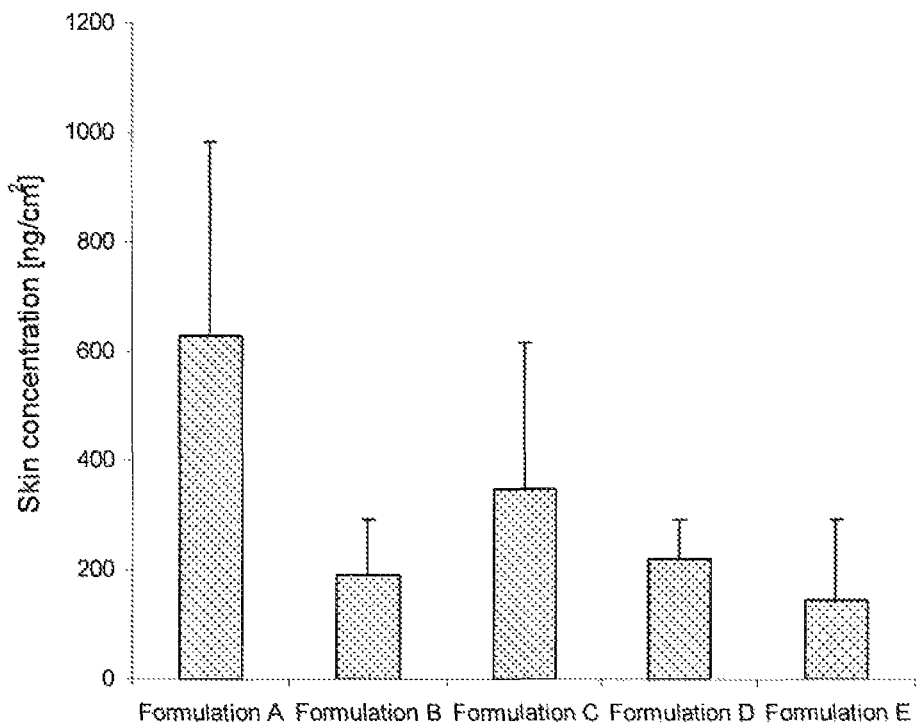
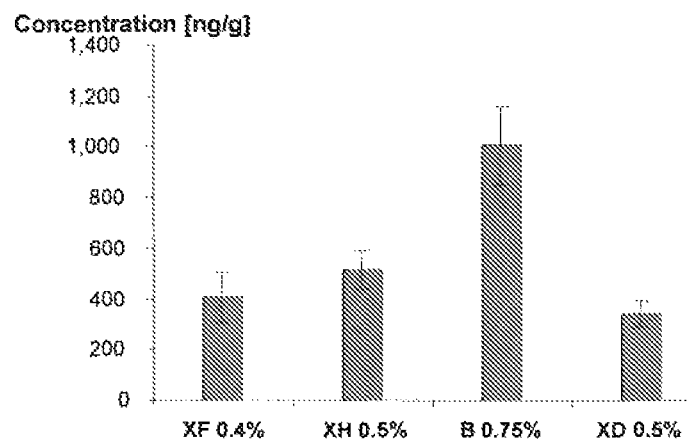

TOPICAL PHARMACEUTICAL COMPOSITION INCLUDING REL-N-[6-[(2R,6S)-2,6-DIMETHYL-4-MORPHOLINYL]-3-PYRIDINYL]-2-METHYL-4'-(TRIFLUOROMETHOXY)-[1,1'-BIPHENYL]-3-CARBOXAMIDE

This is a National Stage of International Application No. PCT/EP2010/060470 filed on Jul. 20, 2010, which claims benefit of U.S. Provisional Application No. 61/227,141 filed Jul. 21, 2009 and U.S. Provisional Application No. 61/295,884 filed Jan. 18, 2010, which in their entirety are herein incorporated by reference.

FIELD OF THE INVENTION

The present invention relates to pharmaceutical compositions of 2-Methyl-4'-trifluoromethoxy-biphenyl-3-carboxylic acid [6-(cis-2,6-dimethyl-morpholin-4-yl)-pyridin-3-yl]-amide, to the use of such compositions in therapeutic applications and to methods for manufacturing such compositions. The invention further relates to a specific form of 2-Methyl-4'-trifluoromethoxy-biphenyl-3-carboxylic acid [8-(cis-2,6-dimethyl-morpholin-4-yl)-pyridin-3-yl]-amide and to the manufacturing and use of such form.

BACKGROUND OF THE INVENTION

WO 2007/131201 and WO 2008/154259 disclose compounds with activity as hedgehog signalling pathway modulators, including 2-Methyl-4'-trifluoromethoxy-biphenyl-3-carboxylic acid [6-(cis-2,6-dimethyl-morpholin-4-yl)-pyridin-3-yl]-amide. Topical pharmaceutical compositions are not specifically disclosed. The disclosures of the publications cited in this specification are herein incorporated by reference in their entirety.

SUMMARY OF THE INVENTION

There is a need to provide a topical pharmaceutical composition comprising 2-Methyl-4'-trifluoromethoxy-biphenyl-3-carboxylic acid [6-(cis-2,6-dimethyl-morpholin-3-yl]-amide which has advantageous properties such as optimum penetration of active compound into the skin, limited systemic exposure, good stability and/or acceptance by the patient. Hence, it is a general object of the invention to provide compositions that possess such desirable properties, and these objectives are achieved by providing a composition as defined herein.

The invention provides in its broadest sense a topical pharmaceutical composition including the compound 2-Methyl-4'-trifluoromethoxy-biphenyl-3-carboxylic acid [6-(cis-2,6-dimethyl-morpholin-4-yl)-pyridin-3-yl]-amide:

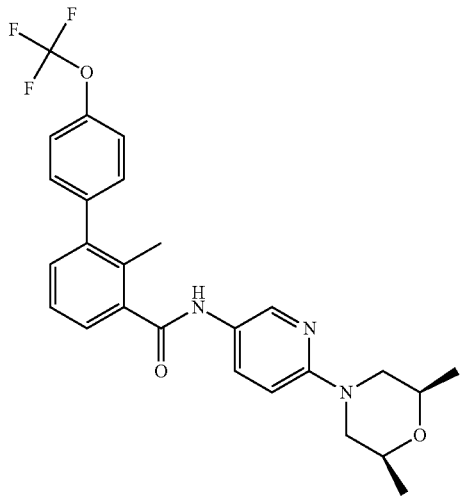 [SMILES: Cc1c(C(=O)Nc2ccc(N3C[C@@H](C)O[C@@H](C)C3)nc2)cccc1-c1ccc(OC(F)(F)F)cc1]

or a solvate thereof ("agent of the invention") and one or more excipients. The agent of the invention is also identified alternatively by the name: rel-N-[6-[(2R,6S)-2,6-dimethyl-4-morpholinyl]-3-pyridinyl]-2-methyl-4'-(trifluoromethoxy)-[1,1'-biphenyl]-3-carboxamide or N-(6-((2S,6R)-2,6-dimethylmorpholino)pyridin-3-yl)-2-methyl-4'-(trifluoromethoxy)biphenyl-3-carboxamide. For the avoidance of doubt, the above mentioned chemical names all refer to the same chemical compound denoted by the above chemical structure and may be used interchangeably.

Such compositions are preferably semi-solid. It was found by the present inventors that such compositions enable delivery of the agent of the invention into the skin in an efficient manner, they limit the systemic exposure by maintaining permeation through the skin at acceptable levels, they benefit from acceptance by the patient, and/or are stable.

Further aspects of the invention are disclosed herein and include a solid form of 2-Methyl-4'-trifluoromethoxy-biphenyl-3-carboxylic acid [6-(cis-2,6-dimethyl-morpholin-4-yl)-pyridin-3-yl]-amide, methods of manufacturing and uses of these compositions. The compositions as described prove to be useful for the treatment of dermatological diseases as defined below.

BRIEF DESCRIPTION OF THE DRAWINGS

FIG. 1 shows the human skin concentrations (penetration) of 2-Methyl-4'-trifluoromethoxy-biphenyl-3-carboxylic acid [6-(cis-2,6-dimethyl-morpholin-4-yl)-pyridin-3-yl]-amide, following application of compositions of the invention.

FIG. 2 shows the levels of 2-Methyl-4'-trifluoromethoxy-biphenyl-3-carboxylic acid [6-(cis-2,6-dimethyl-morpholin-4-yl)-pyridin-3-yl]-amide in de-epidermized pig skin 24 hrs after epicutaneous application of compositions of the invention.

DETAILED DESCRIPTION OF PREFERRED EMBODIMENTS

Figure 3:
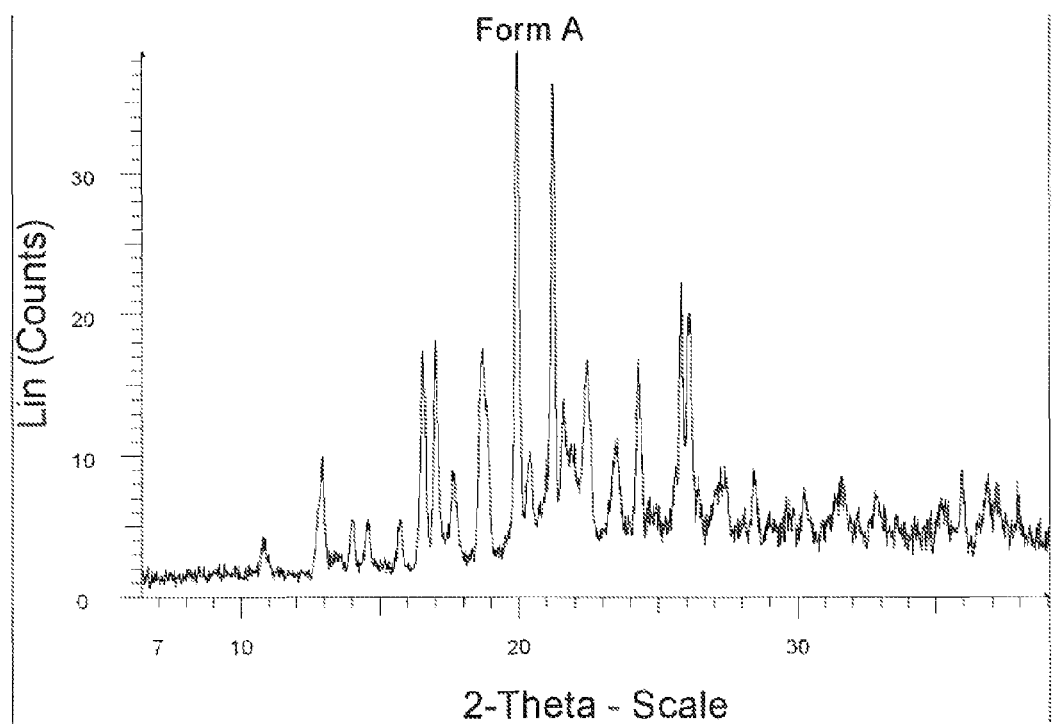
FIG. 3 shows the powder X-ray diffraction pattern of 2-Methyl-4'-trifluoromethoxy-biphenyl-3-carboxylic acid [6-(cis-2,6-dimethyl-morpholin-4-yl)-pyridin-3-yl]-amide, Form A.

The invention may be more fully appreciated and objects other than those set forth above will become apparent when consideration is given to the following description, including the following glossary of terms and the concluding examples.

As used herein, "agent of the invention" means 2-Methyl-4'-trifluoromethoxy-biphenyl-3-carboxylic acid [5-(cis-2,6-dimethyl-morpholin-4-yl)-pyridin-3-yl]-amide, and is intended to represent amorphous and crystalline forms. "Agent of the invention" is intended to also represent a solvate thereof or a prodrug thereof, a pharmaceutical acceptable salt thereof and its mixtures. Preferably, the agent of the invention is 2-Methyl-4'-trifluoromethoxy-biphenyl-3-carboxylic acid [6-(cis-2,6-dimethyl-morpholin-4-yl)-pyridin-3-yl]-amide, present in its freeform, i.e. not as a salt.

As used herein, the terms "including", "containing" and "comprising" are used herein in their open, non-limiting sense. Where the plural form (e.g. compounds, excipients) is used, this includes the singular (e.g. a single compound, a single excipient). "A compound" does not exclude that (e.g. in a pharmaceutical composition) more than one compound (or a salt thereof) is present.

It is further understood that the various embodiments, preferences and ranges of this invention, as provided/disclosed in the specification and claims may be combined at will. Further, depending on the specific embodiment, selected definitions, embodiments or ranges may not apply. The following general definitions shall apply in this specification, unless otherwise specified.

As used herein, the term "solvate" is used herein to describe a molecular complex comprising the compound of the invention and one or more pharmaceutically acceptable solvent molecules, for example, ethanol. The term 'hydrate' employed when said solvent is water.

As used herein, the term "agent of the invention" also includes co-crystals of 2-Methyl-4-trifluoromethoxy-biphenyl-3-carboxylic acid [6-(cis-2,6-dimethyl-morpholin-4-yl)-pyridin-3-yl]-amide, formed with suitable co-crystal formers. These co-crystals may be prepared by known co-crystal forming procedures. Such procedures include grinding, heating, co-subliming, co-melting, or contacting in solution 2-Methyl-4'-trifluoromethoxy-biphenyl-3-carboxylic acid [6-(cis-2,6-dimethyl-morpholin-4-yl)-pyridin-3-yl]-amide with the co-crystal former under crystallization conditions and isolating co-crystals thereby formed. Suitable co-crystal formers include those described in WO 2004/078163.

As used herein, the term "Prodrug" indicates a compound that may be converted under physiological conditions or by solvolysis to a biologically active compound of the invention. Thus, this term refers to a metabolic precursor of an agent of the invention that is pharmaceutical acceptable A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism. Prodrugs of a agent of the invention may be prepared by modifying functional groups present in the agent of the invention in such a way that the modifications are cleaved, either in routine manipulation or in vivo, to the parent compound of the invention. Prodrugs include compounds of the invention wherein a hydroxyl group is bonded to any group that, when the prodrug of the agent of the invention is administered to a mammalian subject, cleaves to form a free hydroxy group. Examples of prodrugs include, but are not limited to, acetate, formate and benzoate derivatives of alcohol groups in the agent of the invention. Suitable prodrugs include pharmaceutically acceptable esters of the agent of the invention. As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms, particularly formates, acetates, propionates, butyrates, acrylates and ethylsuccinates.

As used herein, the term "pharmaceutically acceptable salts" refers to the nontoxic acid salts of the compounds of the invention. These salts can be prepared in situ during the final isolation and purification of the compounds or by separately reacting the base functions with a suitable organic or inorganic acid. Representative salts include, but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methane-sulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluene-sulfonate, and undecanoate.

Also, basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

As used herein, the term "topical pharmaceutical composition" is known in the field (e.g. see European Pharmacopoeia, 6.3, 01/2009, 0132). Such compositions contain (i.e. include, comprise or consist of) i) the agent of the invention and ii) a matrix. The matrix (also referred to as "base") contains pharmaceutically acceptable excipients and is adapted to a topical application. Further, compositions of the invention may be formulated as gel, foam, tincture, (lip) stick, or spray. Consequently, viscosities of the compositions of the invention, may vary over a broad range, typically they are semi-solid or liquid, preferably semi-solid. Compositions of the invention are of the solution type, characterized in that the agent of the invention is dissolved in the matrix. In a preferred aspect the compositions are creams, having the benefit of greater patient acceptability.

According to one aspect, the invention provides a topical pharmaceutical composition including 2-Methyl-4'-trifluoromethoxy-biphenyl-3-carboxylic acid [6-(cis-2,6-dimethyl-morpholin-4-yl)-pyridin-3-yl]-amide and one or more pharmaceutically acceptable excipients.

In another embodiment, the invention provides a topical pharmaceutical composition including:
 a) the agent of the invention;
 b) one or more solvents;
 c) optionally an oily phase;
 d) optionally one or more antioxidants;
 e) optionally one or more consistency improvers
 f) optionally one or more surfactants;

g) optionally one or more preservatives; and
h) optionally one or more gelling agents.

In a further embodiment, the invention provides a topical pharmaceutical composition including:
a) the agent of the invention;
b) one or more solvents;
c) an oily phase;
d) optionally one or more antioxidants;
e) optionally one or more consistency improvers
f) optionally one or more surfactants;
g) optionally one or more preservatives; and
h) optionally one or more gelling agents In another embodiment, the invention provides a topical pharmaceutical composition including:
a) the agent of the invention;
b) dimethylisosorbide (DMI), propylene glycol and optionally one or more further solvents;
c) optionally an oily phase;
d) optionally one or more antioxidants;
e) optionally one or more consistency improvers;
f) optionally one or more surfactants;
g) optionally one or more preservatives; and
h) optionally one or more gelling agents.

In a further embodiment, the invention relates to a composition according to this aspect of the invention which contains one or more additional excipients. Suitable excipients may be selected from the group consisting of antioxidants, gelling agents, ph adjusting agents/buffers, agents to modify consistency, preservatives, (co-)solvents, fillers, binders, disintegrators, flow conditioners, lubricants, fragrances, stabilizers, wetting agents, emulsifiers, solubilizers and salts for regulating osmotic pressure. Such excipients are known in the field, commercially available and may be identified in standard textbooks, such as the Handbook of Pharmaceutical Excipients by R. C. Rowe at al. Such compositions are advantageous to specifically adapt to manufacturers or patients needs and thus improve product properties (like shelf life or patient compliance). Suitable excipients are explained below.

A solvent is an excipient which dissolves the agent of the invention. It is understood that one or more solvents may be used.

A preferred solvent in the compositions of the invention is dimethylisosorbide (DM). In one embodiment, the solvent dimethylisosorbide (DMI) is present in the composition in a range of from 5.0 to 15.0 wt %, preferably at from 7.0 to 13.0 wt %. In a particular embodiment DMI is present at 10.0 wt %.

In another embodiment, the composition further includes the solvent benzyl alcohol. Benzyl alcohol is preferably present in an amount of up to 10 wt %, more preferably in an amount of up to 5 wt %. In preferred embodiments, benzyl alcohol is present in the range of 0.5 to 5 wt %, e.g. in an amount of about 3 wt %.

In another embodiment, the composition further includes the solvent diisopropyl adipate (DIPA). In one embodiment. DIPA is present in the composition in a range of from 10.0 to 20.0 wt %. Preferably, the total amount of DMI and DIPA is up to and including 30.0 wt %. More preferably, DIPA is present at from 12.0 to 18.0 wt % and most preferably DIPA is present at 15.0 wt %.

In another embodiment of the invention, the composition includes the solvent propylene glycol. In one embodiment, propylene glycol is present in the composition at a range of from 0.5 to 20 wt %, and in particular at a range of from 1.0 to 3.0 wt %, more particularly 2.0%. In an alternative embodiment, propylene glycol is present at a range of from 7.0 to 13.0 wt %, particularly 10.0 wt %.

In another embodiment of the invention, the composition includes at least one solvent selected from propylene glycol and DIPA.

In another embodiment of the invention, the composition includes propylene glycol, DIPA or a mixture of propylene glycol and DIPA in a range of 10-35 wt %, preferably in the range of 15-30%, more preferably in the range of 17-25 wt % based on the weight of the composition.

Preferably, according to the invention, the composition includes the solvent dimethylisosorbide (DMI) and an additional solvent selected from: propylene glycol and DIPA. Preferred compositions may contain a mixture of DMI and propylene glycol; a mixture of DMI and DIPA; or a mixture of DMI, propylene glycol and DIPA, in each case optionally together with an additional solvent or solvents.

In another embodiment of the invention an oily phase is present, preferably comprising medium chain triglyceride (MCI). The oily phase is any phase which is not water soluble, and may include excipients such as medium chain triglycerides, paraffin, vaseline, polyalkysiloxane, isopropylmyristate, isopropylpalmitate, isoadipate and vegetable oils/olea herbaria, i.e. castor oil, olive oil. In one embodiment, the oily phase, such as MCT, is present at a range of from 2.0 wt % to 20 wt %. In another embodiment the oily phase is present at from 3.0 wt % to 18 wt %. In one particular aspect of the invention the oily phase is present at 5.0 wt %, and in an alternative is present at 15.0 wt %.

It is understood that one or more antioxidants may be used. In one embodiment the antioxidant is present in the composition and is selected from the group consisting of phenols derivatives (e.g. butylated hydroxytoluene (BHT), butylated hydroxyanisole (BHA)); ascorbic acid derivatives (e.g. ascorbic acid, ascorbyl palmitate), tocopherol derivatives (e.g. Vitamin E, Vitamin E TPGS), bisulfite derivatives (Na bisulfite, Na meta bisulfite) and thio urea. In a particular embodiment the composition includes both butylated hydroxytoluene (BHT) and butylated hydroxyanisole (BHA). A suitable composition may contain up to 2 wt % antioxidant, preferably 0.05-0.5 wt %. In a particular embodiment, the composition includes from 0.05 to 0.15 wt % BHT and from 0.05 to 0.15 wt % BHA. Preferably, the composition includes 0.10 wt % BHT and 0.10 wt % BHA.

Agents to modify consistency, also named consistency improvers, are known in the field, and in another embodiment of the invention the composition includes such agents. It is understood that one or more of such agents may be used, e.g. cetyl alcohol, stearyl alcohol and mixtures thereof. A suitable composition may contain up to 15 wt %, for example from 5.0 to 10.0 wt % in total, of the consistency improver or improvers. In one embodiment, the composition includes the consistency improvers stearyl alcohol and cetyl alcohol. In another embodiment, the consistency improvers steely alcohol and cetyl alcohol are present in equal amounts. In one preferred embodiment, the composition includes steely alcohol in a range of from 2.0 to 6.0 wt % and cetyl alcohol in a range of from 2.0 to 6.0 wt %. In a particular embodiment, stearyl alcohol is present at 4 wt % and cetyl alcohol is present at 4 wt %.

Surfactants are surface active agents. It is understood that one or more surfactants may be used. In an embodiment of the invention, at least one surfactant is present in the composition. In one embodiment, the surfactant or surfactants are present in the range of from 0.5 to 6.0 wt %. In a particular embodiment, the surfactants glyceryl monostearate and sodium cetylstearyl sulfate (Lanette E®) are present in the composition. In one embodiment, glyceryl monostearate is present at from 1.0 wt % to 3.0 wt % and sodium cetylstearyl sulfate (Lanette E®) is present at from 0.1 to 2.0 wt %. In a particular embodiment of the invention, glyceryl monostearate is present at 2.0 wt % and sodium cetylstearyl sulfate (Lanette E®) is present at 1.0 wt %.

It is understood that one or more preservatives may be used. Preservatives are included in the pharmaceutical compositions of this invention to increase shelf life. In one embodiment at least one preservative is present in the composition and is selected from the group of acids (e.g. sorbic acid, benzoic acid); alcohols (e.g. benzyl alcohol), quaternary amines, phenols, and parahydroxybenzoates. In a preferred embodiment the preservative is benzyl alcohol. Benzyl alcohol may also act as a (co)-solvent in the compositions of the invention. In one embodiment the preservative is present in the range of from 0.5 to 5.0 wt %. Preferably, benzyl alcohol is present at 3.0 wt %.

Gelling agents may optionally be included in the compositions of this invention to adjust viscosity. It is understood that one or more gelling agents may be used. For example, gelling agents may be carbomers, acrylic acid derivatives or cellulose derivatives, such as hydroxypropylcellulose. A suitable composition may contain up to 5 wt % gelling agent. In one embodiment, the composition contains from 0.02 to 2.0 wt % gelling agent. In a preferred embodiment, the composition contains 0.5 wt % or 0.2 wt % gelling agent. Preferably, the gelling agent is carbomer 974P.

Agents to adjust the pH or to provide a pH buffer are known in the field. It is understood that one or more of such agents may be used, such as sodium hydroxide. A suitable composition may contain such acids/bases to adjust the pH of the inventive composition in the range of 4-8, preferably 5-7, such as 6.5.

The amount of agent of the invention in the inventive composition may vary over a broad range, it is typically provided in an effective amount. An effective amount refers to an amount of the agent of the invention which, when administered to a mammal, particularly a human, is sufficient to effect a treatment as defined below. Suitable amounts for the agent of the invention may be determined by the skilled person in routine experiments; typically they are in the range between 0.2-5 wt-%, preferably 0.5-2.0 wt-%, such as 0.25, 0.5, 0.75 or 1.0 wt % of the total composition.

The invention relates in another aspect to a method for manufacturing compositions as described herein comprising the steps of:

1. combining the lipophilic excipients as described herein to obtain a lipophilic phase, combining this phase with the agent of the invention, and melting the mixture.
2. combining the hydrophilic excipients and heating
3. combining the hydrophilic and lipophilic phases, then adjusting the pH.

A composition according to this invention may be prepared by processes that are known per se, but not yet applied for the present compositions where they thus form new processes. In general, the manufacture of a pharmaceutical composition comprises the step of combining the agent of the invention with a matrix, e.g. by mixing, dissolving and/or lyophilizing. Such steps may also comprise heating or cooling the materials used. The agent of the invention is available according to known processes or according to processes as described herein; the individual components of the matrix are either known per se or available according to known processes.

In one embodiment, the invention relates to a method of manufacturing a composition as described herein comprising the steps of combining all liquid non-aqueous excipients and the agent of the invention and optionally heating the mixture to 30-95° C. to obtain a solution, melting the solid excipients at a temperature between 30-95° C. to obtain a melt, combining the solution and melt, preferably at a temperature between 30-95° C., optionally adding water or an aqueous phase to the combined mixture optionally cooling down the obtained composition.

The invention relates in another aspect to the use of such compositions as a pharmaceutical, particularly as a pharmaceutical for the use of dermatological diseases.

Compositions comprising 2-Methyl-4'-trifluoromethoxy-biphenyl-3-carboxylic acid [6-(cis-2,6-dimethyl-morpholin-4-yl)-pyridin-3-yl]-amide are suitable for the treatment, including prophylaxis and delay of progression, of diseases related to modulation of activity of the hedgehog signaling pathway. In particular, the compositions herein are useful for the treatment of dermatological diseases. The term "dermatological diseases" as used herein includes all types of dermatological diseases, disorders or conditions in a mammal (in particular a human). In one particular embodiment of the invention, the compositions disclosed herein are useful to treat diseases or conditions including hyperproliferative skin conditions such as basal cell nevus syndrome (also called Gorlin's syndrome and/or nevoid basal cell carcinoma), a rare autosomal dominant genetic syndrome leading to cancers such as skin cancers, basal cell carcinoma (BCC). In particular superficial basal cell carcinoma (sBCC) and nodular basal cell carcinoma, sebaceous hyperplasia and psoriasis.

Thus in one embodiment of the invention, the invention provides a composition as described herein for use in medicine. In another embodiment, the invention provides a composition for use in treating a dermatological disease disorder or condition mediated by the hedgehog signaling pathway. In a further embodiment, the invention provides a composition for use in treating a hyperproliferative skin condition, or a dermatological disease, disorder or condition selected from Gorlin's syndrome, basal cell carcinoma, sebaceous hyperplasia and psoriasis.

In another embodiment, the invention provides the use of a composition as described herein for the manufacture of a medicament for the treatment of a dermatological disease, disorder or condition mediated by the hedgehog signaling pathway. In a further embodiment, the invention provides the use of a composition as described herein for the manufacture of a medicament for the treatment of a hyperproliferative skin condition, or a dermatological disease, disorder or condition selected from Gorlin's syndrome, basal cell carcinoma, sebaceous hyperplasia and psoriasis.

In another embodiment, the invention relates to a method of treatment of a dermatological disease, disorder or condition mediated by the hedgehog signaling pathway (particularly selected from the group consisting of a hyperproliferative skin condition, or Gorlin's syndrome, basal cell carcinoma, sebaceous hyperplasia and psoriasis), which treatment comprises administering to a subject in need of such treatment, particularly a human, an effective amount of a composition as described herein.

In a further embodiment, the invention relates to a method as described herein, wherein a composition as described herein is administered in combination with another pharmaceutically acceptable composition, either simultaneously or in sequence.

For treatment using a composition of the invention, the appropriate dosage will, of course, vary depending upon, for example, the type of composition used, the individual host and the nature and severity of the conditions being treated. However, in general, for satisfactory results in larger mammals, for example humans, an indicated daily dosage is in the range from about 0.01 g to about 1.0 g, of a compound of the present invention; conveniently administered, for example, in divided doses up to four times a day.

The invention relates in another aspect to specific forms of the agent of the invention.

In one embodiment, the invention relates to 2-Methyl-4'-trifluoromethoxy-biphenyl-3-carboxylic acid [6-(cis-2,6-dimethyl-morpholin-4-yl)-pyridin-3-yl]amide in crystalline form.

Particularly, the invention relates to the polymorphic form A as defined herein, substantially free of other polymorphic forms of the agent of the invention. In a further embodiment, the invention relates to 2-Methyl-4'-trifluoromethoxy-biphenyl-3-carboxylic acid [6-(cis-2,6-dimethyl-morpholin-4-yl)-pyridin-3-yl]-amide form A comprising the following X-ray powder diffraction peaks: 2-theta values 12.9, 16.5, 17.0, 18.8, 19.9, 21.2, 22.4, 24.3, 25.8 and 26.1. Form A is produced following the synthetic methods described herein.

The invention further relates to the polymorphic form B as defined herein, either substantially free of other polymorphic forms of the agent of the invention or in a mixture with other polymorphic forms of the agent of the invention. Form B is produced following the synthetic methods described herein.

The invention further relates to the amorphous form of the agent of the invention as described herein.

FIG. 3 shows the powder X-ray diffraction pattern of polymorph A. Relative intensities are dependent on several factors including particle size, shape and method of sample preparation, thus are subject to variation. The data was obtained using the instrument Scintag INC, irradiation CuKα (45 kV, 40 mA), continuous scan, scan rate 0.5°/min (2 theta value), scan range 1.5°-40° (2 theta value).

In a further embodiment, the invention relates to the agent of the invention obtainable by or obtained by a process as described herein.

MODES FOR CARRYING OUT THE INVENTION

The following Examples serve to illustrate the invention without limiting the scope thereof. It is understood that the invention is not limited to the embodiments set forth herein, but embraces all such forms thereof as come within the scope of the disclosure.

A. Synthesis of N-(6-((2S,6R)-2,6-dimethylmorpholino)pyridin-3-yl)-2-methyl-4'-(trifluoromethoxy)biphenyl-3-carboxamide

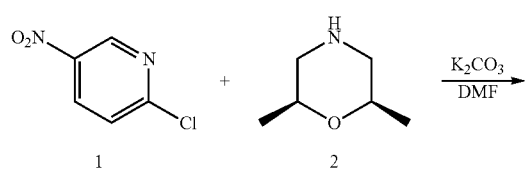

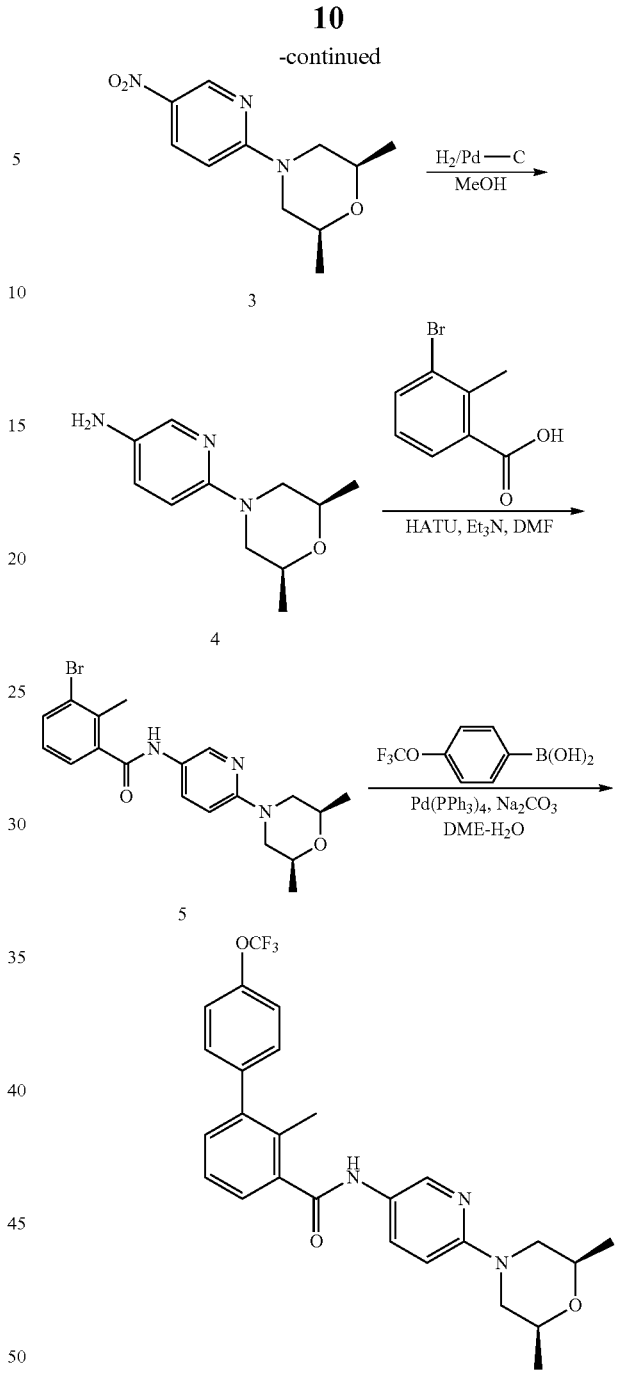

Step 1: To a solution of 2-chloro-5-nitro-pyridine 1 (5.58 g, 35.2 mmoL) and cis-2,6-dimethylmorpholine (4.05 g, 35.2 mmoL) in anhydrous DMF (30 mL) was added K$_2$CO$_3$ (9.71 g, 70.4 mmoL). The mixture was heated at 50° C. overnight. After concentration, the residue is partitioned between EtOAc and water. The EtOAc layer is dried over anhydrous Na$_2$SO$_4$ and concentrated to give crude product 3 as a yellow solid, after purification by silica gel chromatography, obtained pure product (7.80 g, 93.2%), LC-MS m/z: 238.2 (M+1).

Step 2: The above material 3 (7.30 g, 30.8 mmoL) was hydrogenated in the presence of 10% Pd—C (1.0 g) in MeOH (120 mL) under hydrogen overnight. The suspension was filtered through celite and the filtrate was concentrated to give the crude product 4 (5.92 g) as a dark brown oil which was used directly in the next step without further purification. LC-MS m/z: 208.2 (M+1).

Step 3: To a solution of 3-bromo-2-methyl benzoic acid (2.71 g, 12.6 mmoL), 6-((2S,6R)-2,6-dimethylmorpholino) pyridin-3-amine 4 (2.61 g, 12.6 mmoL), and HATU (4.80 g, 12.6 mmoL) in anhydrous DMF (30 mL) was added diisopropylethylamine (6.58 mL, 37.8 mmoL) dropwise. The resulting mixture was stirred overnight at room temperature. The reaction mixture was diluted with water (50 mL), and then extracted with EtOAc (3×120 mL). The organic layer was dried and concentrated to give the crude product. This crude product was then purified by flash column chromatography using 30% EtOAc in hexane as eluent to give 5 as a white solid (4.23 g, 83.0%), LC-MS m/z: 404.1 (M+1).

Step 4: A mixture of 4-(trifluoromethoxy)phenylboronic acid (254 mg, 1.24 mmol), 3-bromo-N-[6-(2,6-dimethyl-morpholin-4-yl)-pyridin-3-yl]-4-methyl-benzamide 5 (250 mg, 0.62 mmol), Pd(PPh$_3$)$_4$ (36 mg, 0.03 mmol), Na$_2$CO$_3$ (2.0M aqueous solution, 1.23 mL, 2.4 mmol) and DME (4.5 mL) in a sealed tube was heated at 130° C. overnight. The reaction mixture was diluted with EtOAc and water. The aqueous layer was extracted with EtOAc. The combined organic layer was washed with brine and concentrated to give the crude product which was then purified by preparative mass triggered HPLC (C$_{18}$ column, eluted with CH$_3$CN—H$_2$O containing 0.05% TFA) to give N-(6-((2S,6R)-2,6-dimethylmorpholino)pyridin-3-yl)-2-methyl-4'-(trifluoromethoxy)biphenyl-3-carboxamide (183.5 mg, 61.1% yield). LC-MS m/z: 486.2 (M+1).

The resultant crystalline product (Form A) was converted to the amorphous form by dissolving in 3% w/w aqueous ethanol, and the resultant solution spray dried at about 150° C.

Form B was prepared by heating the amorphous form in an oven at 110° C. for 2 hours.

In a further embodiment, the invention relates to a process step or steps, or an intermediate described herein.

B Pharmaceutical Compositions

Test formulations of the invention (creams, solution type)

| Formulation code Composition | Form B [%] | Form C [%] | Form D [%] | Form E [%] |
|---|---|---|---|---|
| Propylene Glycol | 10.00 | 2.00 | 10.00 | 2.00 |
| Diisopropyl adipate(DIPA) | 15.00 | 15.00 | 15.00 | 15.00 |
| Dimethyl isosorbide(DMI) | 10.00 | 10.00 | 10.00 | 10.00 |
| Benzyl alcohol | 3.00 | 3.00 | 3.00 | 3.00 |
| Butylhydroxyanisol | 0.10 | 0.10 | 0.10 | 0.10 |
| Butylhydroxytoluol | 0.10 | 0.10 | 0.10 | 0.10 |
| Triglyceride (MCT) | 15.00 | 5.00 | 5.00 | 5.00 |
| Stearyl alcohol | 4.00 | 4.00 | 4.00 | 4.00 |
| Cetyl alcohol | 4.00 | 4.00 | 4.00 | 4.00 |
| Glyceryl monostearate | 2.00 | 2.00 | 2.00 | 2.00 |
| Active compound* | 0.75 | 0.75 | 0.75 | 0.25 |
| Sodium cetylstearyl sulfate (Lanette E ®) | 1.00 | 1.00 | 1.00 | 1.00 |
| Carbopol 974P | X | 0.50 | 0.20 | 0.50 |
| Nanopure water | 35.05 | 48.65 | 43.15 | 49.15 |
| Sodium Hydroxide 1M | X | 3.90 | 1.70 | 3.90 |
| Total | 100.00 | 100.00 | 100.00 | 100.00 |

Comparator Formulations:

| formulation XD (cream solution type) Excipient | Amount [%] |
|---|---|
| Active compound* | 0.5 |
| medium chain triglyceride (MCT) | 20 |
| Sodium cetylstearyl sulfate | 1 |
| Cetyl alcohol | 4 |
| Stearyl alcohol | 4 |
| Glycerolmonostearat | 2 |
| Benzyl alcohol | 5 |
| Polysorbate 80 | 2 |
| Water | 61.5 |

| Formulation XF (cream solution type) Excipient | Amount [%] |
|---|---|
| Active compound* | 0.4 |
| medium chain triglyceride (MCT) | 20 |
| DIPA | 15 |
| Transcutol | 10 |
| Sodium cetylstearyl sulfate | 1 |
| Cetyl alcohol | 4 |
| Stearyl alcohol | 4 |
| Glycerolmonostearat | 2 |
| Benzyl alcohol | 1 |
| Butylated hydroxytoluene | 0.1 |
| Water | 42.5 |

| Formulation XH (cream solution type) Substance | Amount [g] |
|---|---|
| Mid chain triglycerides | 5 |
| Di isopropyl adipate | 15 |
| Propylene glycol | 10 |
| Oleyl alcohol | 10 |
| Sodium cetylstearyl sulfate | 1 |
| Cetyl alcohol | 4 |
| Stearyl alcohol | 4 |
| Glycerol monostearat | 2 |
| Benzyl alcohol | 3 |
| BHT | 0.1 |
| BHA | 0.1 |
| Active compound* | 0.5 |
| Water | 45.3 |

*active compound means 2-Methyl-4'-trifluoromethoxy-biphenyl-3-carboxylic acid [6-(cis-2,6-dimethyl-morpholin-4-yl)-pryidin-3-yl]-amide In Vitro Human Skin Penetration/Permeation Assay Ca. 300 mg or 300 µL of formulation were applied on each skin punch (thawed samples of human abdominal cadaver skin dermatomized to a thickness of 500 µm). The integrity of the skin was determined by evaluating the permeation of tritiated water. Formulations were tested on skin samples having similar $^3$H$_2$O permeation. The receptor chamber was filled with a mixture of phosphate buffered saline and fetal bovine serum (2+1, v/v; pH=7.4) as receiver solution (Gibco BRL, CH) to simulate the human physiological conditions and the systemic removal of the drug from skin. The receiver solution contained 100 U/mL of 1% penicilline/strepto-mycine mixture to prevent microbiological contamination. The temperature of the cells was kept at 34±1° C.

200 µL of receiver solution was sampled/cell and replaced at each occasion with the same volume of blank solution in order to keep the total buffer volume constant during the assay period. The time points investigated were 4, 7, 20, 24, 28, 32, 44 and 48 h after application.

At the end of the experiment, the residual formulation on the surface of each skin sample was removed. The stratum corneum was separated from the epidermis/dermis by 20 strippings, and biopsies of the treated area of the stripped skin were taken. The drug content in the receptor fluids and stripped skin was assessed by LC/MS/MS.

The flux was calculated by linear regression analysis from the slope of the linear portion of the concentration-vs.-time plot in addition, the cumulative drug amount permeated was assessed.

FIG. 1 shows the skin concentrations (penetration), where formulation A is a reference formulation of 1.0% active compound in ethanol/PEG (polyethylene glycol) 30/70.

Formulations B, D and E give similar, good skin penetration levels. Unexpectedly, following application of formulation C, even higher skin penetration levels are obtained.

The following formulations XD, XF and XH were also tested against formulation B in the in-vitro human skin penetration assay. The results show that all the tested formulations provide acceptable skin penetration levels, however formulation B provides an unexpectedly good level of skin penetration.

| Formulation | Skin concentration after 48 h (ng/cm$^2$) | Skin concentration after 48 h (ng/g) |
|---|---|---|
| XD | 55 | 860.0 |
| XF | 132 | 1690.0 |
| XH | 60 | 910.0 |
| B | 168 | 2120.0 |

In Vivo Tests

1. Test for Penetration into the Skin of Domestic Pigs ("4 cm$^2$ assay")

Method: The "4 cm$^2$ assay" is used to measure the time-dependent penetration of an epicutaneously applied compound into the dermis of juvenile domestic pigs. The animals (weighing 12-18 kg) are placed in a humane restraint sling for treatment. The pharmaceutical compositions, solution type, as prepared above, were applied once to different small areas (4 cm$^2$) on the dorsolateral back at 8, 6, 4, 2, 1 and 0.5 hrs prior to euthanasia and dissection of the treated skin samples. Next, heated metal blocks were placed on the treated skin flaps for 1 min and the loosened epidermis was peeled off with forceps. From the de-epidermized skin flap 1 mm thick dermal sheets were prepared with a dermatome from which 6 mm punch biopsies were collected and analysed for time-dependent test compound concentration by LC/MS. The procedure described was done with careful avoidance of contamination of the dermal samples with superficially attached test compound.

Results: The following table provides Area Under the Curve (AUC) values of the agent of the invention in pig dermis when applied epicutaneously in the identified compositions.

| Formulation | AUC 0-8 h [µg*h/g] Mean (SEM)+ |
|---|---|
| B (0.75%) | 2.0 (0.47) |
| C (0.75%) | 3.0 (0.87) |
| D (0.75%) | 3.1 (0.68) |

+Values from 8 dermal samples per formulation and time point (4 pigs, 2 samples each)

The results of the "4 cm$^2$ assay" confirm the good penetration into the skin of the agent of the invention following application of compositions B, C and D under in-vivo-conditions.

FIG. 2 shows the levels of active compound in de-epidermized pig skin 24 hrs after epicutaneous application of different formulations. Following application of Formulation B, an unexpected improvement in the dermal concentration of active compound is observed, compared to the comparator formulations. The levels are dose-proportionally high.

| Formulation | Compound levels in pig dermis 24 hrs after application (ng/g) Mean (SEM)+ |
|---|---|
| XF 0.4% | 407 (97') |
| XH 0.5% | 517 (77) |
| B 0.75% | 1,007 (153) |
| XD 0.5% | 340 (52) |

+Mean of 6 samples per formulation (3 animals, 2 dermal samples each)

2. Test for Permeation Through the Skin of Domestic Pigs (10% BSA-Assay)

Method: The primary objective of the "10% BSA-assay" is to assess the percutaneous absorption (permeation through the skin) of a formulated compound after application to 10% body surface area (BSA) in juvenile, 12-18 kg weighing pigs. In addition, dermal levels of the treated skin are determined at termination (24 his after application). The formulation is applied in volumes of 5 ml to 400 cm$^2$ dorsal area (equivalent to 10% BSA of a 10 kg animal Blood samples are collected from a jugular vein 0.5, 1, 2, 4, 8, and 24 hrs after the application. Dermal samples from the treated skin are prepared as described.

Results: After application of formulations XF (0.45%), XH (0.5%), XD (0.5%) and 8 (0.75%) levels of active compound were in most plasma samples below LLOQ (0.1 ng/ml). The fewest positive samples with the lowest levels were detected in XH and B-treated animals. Highest and most frequent levels were detected in XD-treated animals. The levels were 0.29 (SEM:0.11) and 0.08 (SEM: 0.04) ng/ml at 0.5 and 1 hrs after application, respectively. At later time points the levels were below LLOQ.

3. Test for Efficacy in Treatment of BCCs (Basal Cell Carcinomas)

Methods: A total of 8 Gorlin's Syndrome patients, presenting 27 BCCs, were treated b.i.d. with Formulation B or with vehicle for 4 weeks. The vehicle is a formulation equivalent to Formulation B except that the active compound is replaced by an equivalent percentage of water.

Results: The Formulation B was well tolerated and showed no potential for skin irritation. Plasma concentrations of the active compound after 4 weeks' treatment were below detection level (0.05 ng/mL) in 4/8 patients (highest plasma level detected was 0.11 ng/mL). Mean skin concentrations of the active compound were 737 ng/g (BCC) and 605 ng/g (uninvolved skin). BCCs treated with the Formulation B (n=13) showed complete clinical response in 3, partial response in 9 and no response in 1 BCC. Except for one partial response, the vehicle produced no clinical response in any of the 14 treated BCC's.

Mean volume reductions of 49.8% were observed in the BCCs treated with Formulation B vs. 9.1% with the vehicle treatment, mean surface area reductions were 40.8% and 10.5%, respectively (3D digital photography). Histologically, the residual tumor cells nests showed an average 60% reduction of Ki-67 proliferating cells in the lesions treated with Formulation B vs. vehicle. Biomarker analysis showed that, except for one patient, Gli 1, Gli 2, Ptch 1 and Ptch 2 mRNA level reductions correlated with clinical outcome.

Conclusions

These results demonstrate that the formulations of the invention are effective in the treatment of BCCs in Gorlin's Syndrome patients. Since the use of other currently available topicals for treatment of BCCs is limited by skin irritation, treatment with formulations of the present invention in NBCCS patients may offer a significant and unexpected advantage.

The invention claimed is:

1. A crystalline polymorph Form A of 2-methyl-4'-trifluoromethoxy-biphenyl-3-carboxylic acid [6-(cis-2,6-dimethyl-morpholin-4-yl)-pyridin-3-yl]-amide that exhibits an X-ray powder diffraction pattern having characteristic peaks expressed in degrees 2-theta at 12.9, 16.5, 17.0, 18.6, 19.9, 21.2, 22.4, 24.3, 25.8 and 26.1.

2. The crystalline polymorph Form A of claim 1 as characterized by the X-ray powder diffraction pattern of FIG. 3.

3. A pharmaceutical composition comprising the crystalline polymorph Form A according to claim 1 and an excipient.

* * * * *